US012085537B2

(12) United States Patent
Alberts et al.

(10) Patent No.: US 12,085,537 B2
(45) Date of Patent: Sep. 10, 2024

(54) ENERGY EFFICIENT SIMPLIFIED ANALOGUE PHASED ARRAY TRANSDUCER FOR BEAM STEERING

(71) Applicant: NovioScan B.V., Nijmegen (NL)

(72) Inventors: Bastianus Theodorus Johannes Alberts, Nijmegen (NL); Reinout Woltjer, Nijmegen (NL)

(73) Assignee: NovioScan B.V., Nijmegen (NL)

( * ) Notice: Subject to any disclaimer, the term of this patent is extended or adjusted under 35 U.S.C. 154(b) by 383 days.

(21) Appl. No.: 17/435,818

(22) PCT Filed: Mar. 6, 2020

(86) PCT No.: PCT/NL2020/050145
§ 371 (c)(1),
(2) Date: Sep. 2, 2021

(87) PCT Pub. No.: WO2020/180184
PCT Pub. Date: Sep. 10, 2020

(65) Prior Publication Data
US 2022/0146461 A1 May 12, 2022

(30) Foreign Application Priority Data

Mar. 6, 2019 (NL) ..................................... 2022682

(51) Int. Cl.
*G01N 29/26* (2006.01)
*A61B 8/00* (2006.01)
*G01N 29/06* (2006.01)
*G01N 29/24* (2006.01)

(52) U.S. Cl.
CPC .......... *G01N 29/262* (2013.01); *A61B 8/4227* (2013.01); *A61B 8/4254* (2013.01); *A61B 8/4488* (2013.01); *G01N 29/0654* (2013.01); *G01N 29/245* (2013.01)

(58) Field of Classification Search
CPC ............. G01N 29/262; G01N 29/0654; G01N 29/245; G01N 2291/106; A61B 8/4227; A61B 8/4254; A61B 8/4488; A61B 8/5223
See application file for complete search history.

(56) References Cited

U.S. PATENT DOCUMENTS

| | | | |
|---|---|---|---|
| 2005/0096545 A1* | 5/2005 | Haider | G01S 15/8925 600/447 |
| 2006/0079779 A1* | 4/2006 | Takimoto | G01S 7/52038 600/447 |
| 2017/0100092 A1 | 4/2017 | Kruse et al. | |

(Continued)

FOREIGN PATENT DOCUMENTS

| | | |
|---|---|---|
| EP | 3384851 A1 | 10/2018 |
| WO | 2019/030282 A1 | 2/2019 |

*Primary Examiner* — Xin Y Zhong
(74) *Attorney, Agent, or Firm* — N.V. Nederlandsch Octrooibureau

(57) ABSTRACT

The present invention relates in a first aspect to an energy efficient simplified analogue phased array transducer for ultrasound beam steering, in a second aspect to a product, such as a small wearable ultrasound device for signalling changes in a human or animal body, such as a liquid volume in a body cavity of a human or an animal, in a third aspect to a use of said device, and in a fourth aspect to a method of operating an ultrasound device.

20 Claims, 5 Drawing Sheets

(56) References Cited

U.S. PATENT DOCUMENTS

| | | |
|---|---|---|
| 2017/0258386 A1* | 9/2017 | Woltjer .................... A61F 5/48 |
| 2018/0092630 A1 | 4/2018 | Duerr et al. |
| 2020/0015787 A1* | 1/2020 | Watanabe ........... G01S 15/8997 |
| 2020/0191928 A1* | 6/2020 | Hope Simpson ... G01S 7/52034 |

* cited by examiner

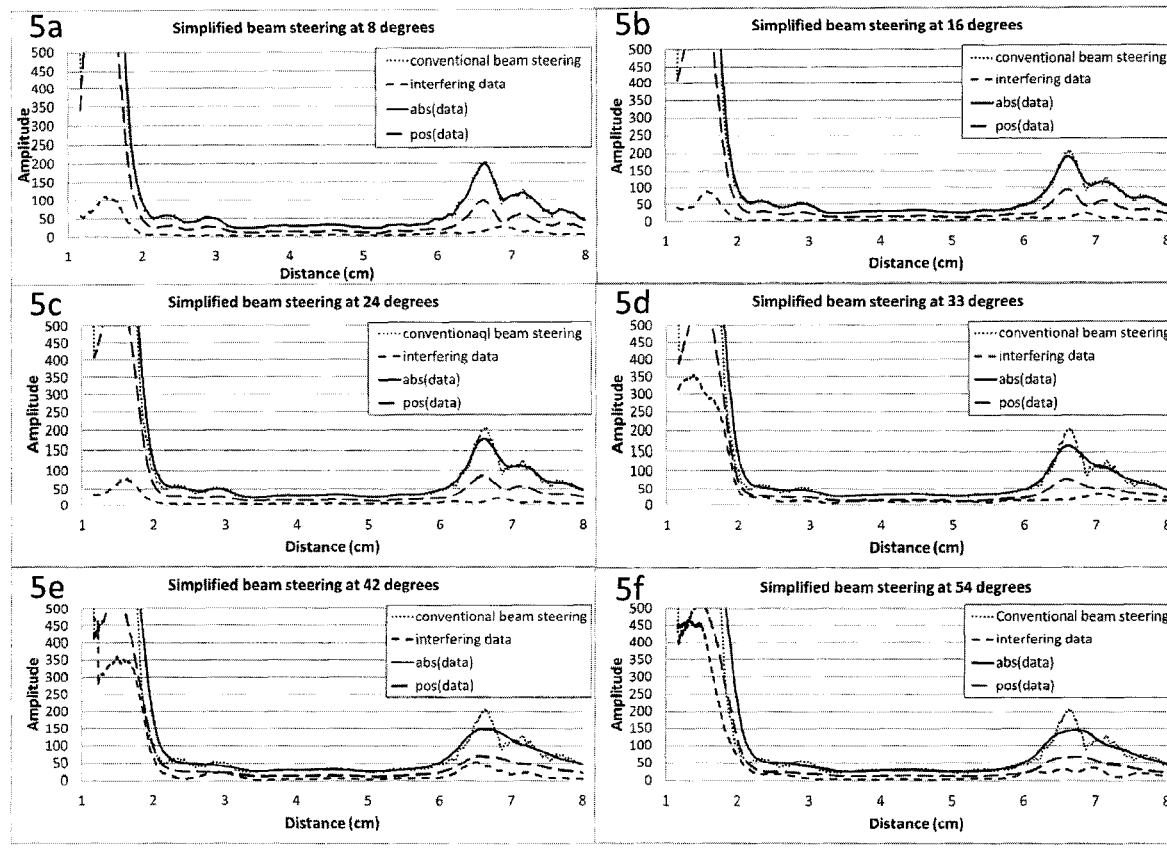
Fig. 5a-f
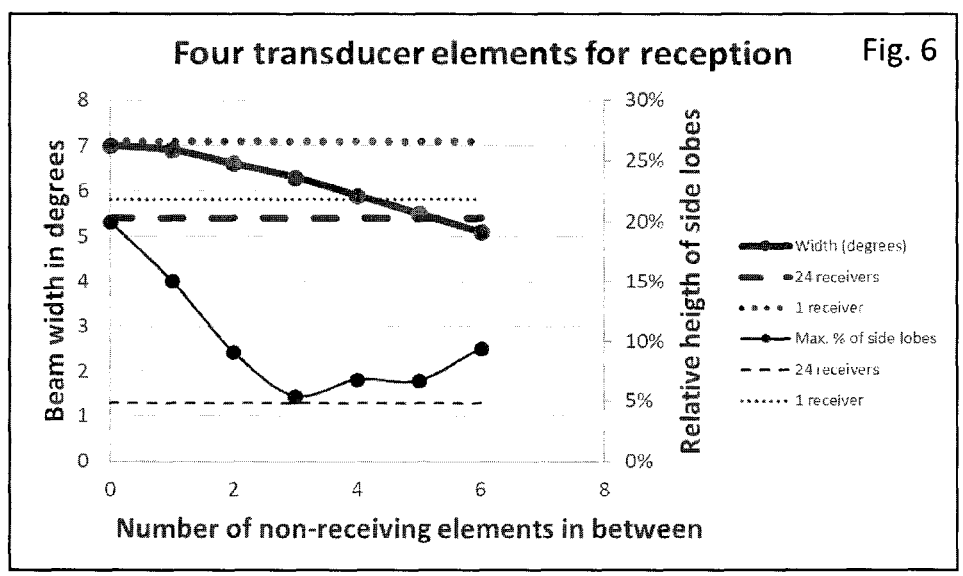

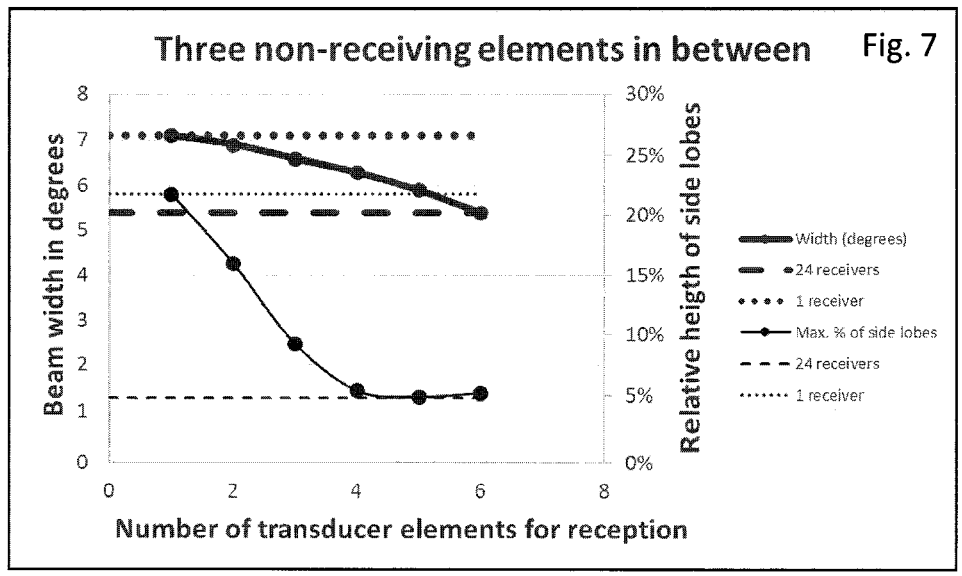
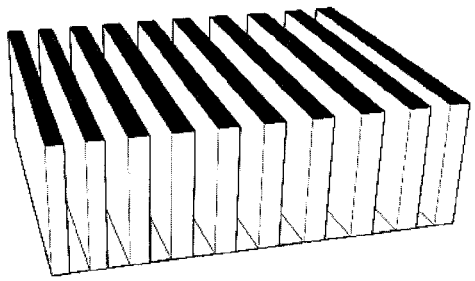
Fig. 8a
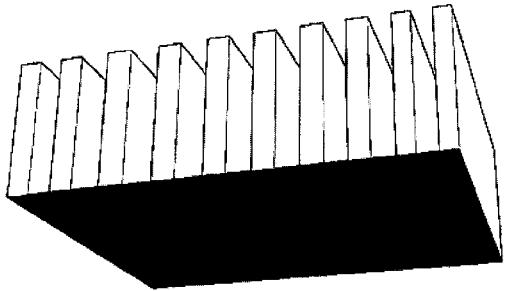
Fig. 8b
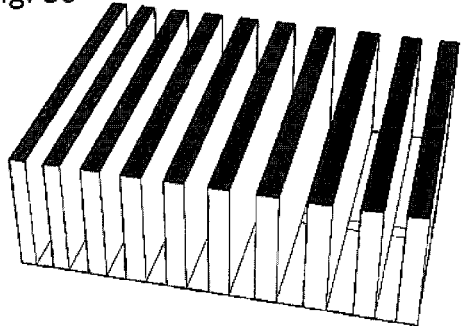
Fig. 8c
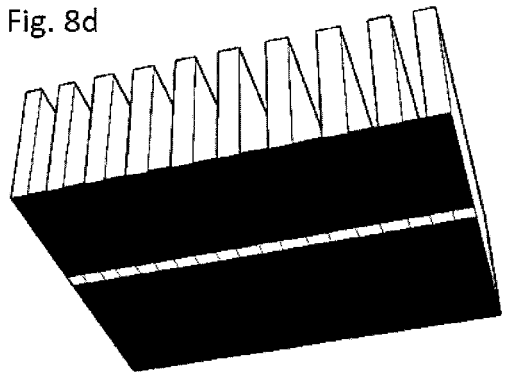
Fig. 8d

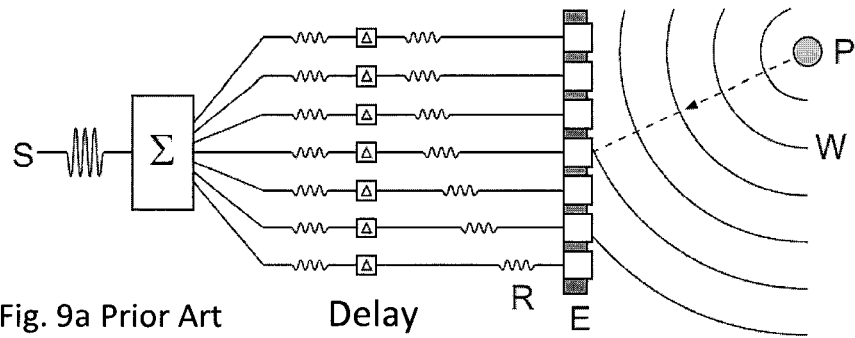
Fig. 9a Prior Art  Delay
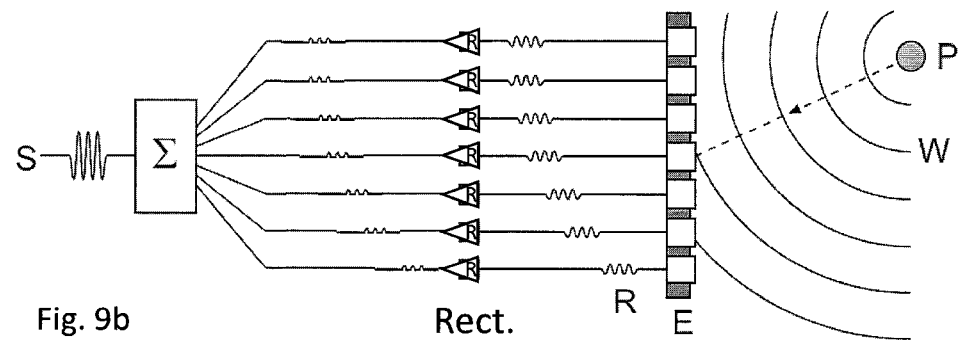
Fig. 9b  Rect.
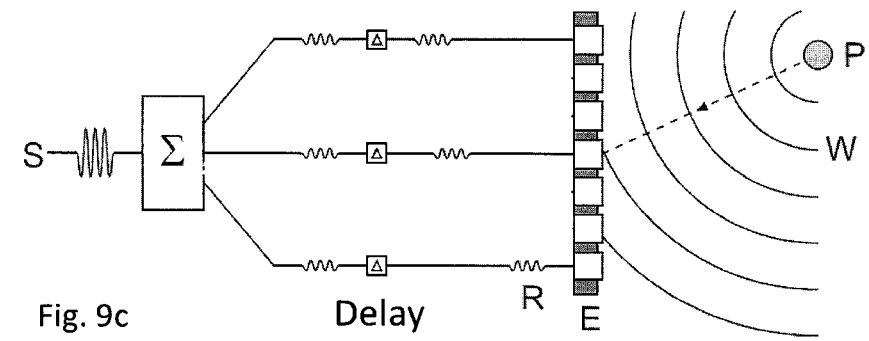
Fig. 9c  Delay
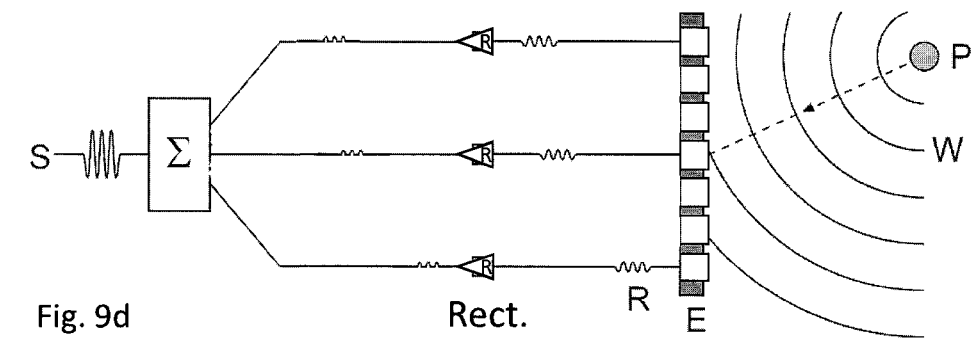
Fig. 9d  Rect.

ENERGY EFFICIENT SIMPLIFIED ANALOGUE PHASED ARRAY TRANSDUCER FOR BEAM STEERING

FIELD OF THE INVENTION

The present invention is in the field of an energy efficient simplified analogue phased array transducer for ultrasound beam steering, such as for a small wireless ultrasound device for signalling a change in a body tissue, body vessel or body cavity, such as a bladder, comprising said transducer array, use of said device for determining or monitoring a liquid volume in a cavity, and a method of operating said device.

BACKGROUND OF THE INVENTION

Ultrasound is an oscillating sound pressure wave with a frequency greater than the upper limit of the human hearing range (hence ultra-sound). Ultrasound devices may operate with frequencies from 20 kHz up to several gigahertz. The wavelength of the ultrasound typically refers to the wavelength of the ultrasound in the medium wherein the ultrasound travels, at the operating frequency of the ultrasound transducer. Physics indicate that the wavelength in the medium is the operating frequency divided by the speed of sound in the medium (approximately 1500 m/s in human tissue). Ultrasound may be used in many different fields. Ultrasonic devices are used to detect objects and measure distances. Ultrasonic imaging (sonography) is used in both veterinary medicine and human medicine. In the non-destructive testing of products and structures, ultrasound is used to detect invisible flaws. Industrially, ultrasound is used for cleaning and for mixing, and to accelerate chemical processes. Ultrasound can be used for medical imaging, detection, measurement and cleaning. At higher power levels, ultrasound may be useful for changing the chemical properties of substances.

There have been approaches to improve ultrasound systems in terms of size, cost, and quality, such as transducer design, transmit and receive circuitry design, and beamforming algorithms. Currently, a significant percentage of the size and power of an ultrasound system is devoted to the beamformer, which is responsible for directing and/or focusing the ultrasound beam. A standard beamformer, which may comprise 64 to 128 transmit/receive channels, may be straight-forward to implement if design constraints such as size and power are relaxed. As ultrasound systems become more portable, however, it seems necessary that beamformer architectures with lower power consumption than standard cart-based systems are required, especially for applications where image quality is less critical.

An application of ultrasound concerns bladder monitoring. Many people such as elderly persons, children with dysfunctional voiding or bedwetting, women after delivery of a baby, patients with a neurogenic bladder, dement people, and others, have a difficulty to control functioning of the bladder, and to be at the toilet on time to urinate. This (partial) incontinency is highly inconvenient and may lead to psycho-logical problems and physical problems (e.g. infection, local skin problems). Solutions to this incontinency relate to applications of e.g. diapers and bedwetting alarms. However, such are effectively not more than limiting consequences of incontinency, without providing a real solution, and still a bad odour, and wet pants/dresses cannot be prevented. Such solutions also cost a considerable amount of money, in terms of diapers and time of care and the pollution by the diapers after use is significant.

For some ultrasound applications, such as bladder monitoring, often dedicated devices are used. These dedicated devices may suffer from one or more drawbacks, amongst others a need of a wire between transducer and monitor, handheld use of the device; hence they are not suited for long-term monitoring. Some prior art devices may even require a trained professional to handle the transducer and to evaluate what is seen. Typically, these are used for intermittent examinations in a healthcare setting such as a hospital. With such technologies it is not possible to keep continuous track of bladder filling and alarm a user or his/her caretaker when the bladder becomes full. That is relevant for a number of (health) problems, including, but not limited, to Urinary Incontinence (UI) in children (hypo- or hyperactive bladder, dysfunctional voiding, bedwetting); adults with neurogenic bladder dysfunction, people with temporary or permanent spinal problems, in nursing home patients. It is also relevant for the prevention of Urinary Retention (UR) (e.g. peri- and post-operatively, post-partum).

Ultrasound devices are typically hand-held and built for intermittent use and are large, or at least too large to be wearable, they cannot be fixed to the body (semi-)permanently, cannot be used by a patient during normal life, during sitting, standing or lying down, and may require cabling for power- and signal transport, and are not practical in use.

In principle ultrasound could be used to monitor and determine an amount of fluid, such as being present in a human body. Such is typically only possible with prior art devices that are handheld, but not wearable. One of the implications is that current ultrasound devices are used intermittently, and the patient cannot move during a monitor procedure, and therefore require very well-defined situations. Such is at least problematic in most other, practically occurring, situations, such as a sequence of sitting, standing and lying down.

In an example thereof, US 2017/100092 A1 recites a system for acquiring and providing information about orthopedic features of a body using acoustic energy. The electronics are considered background prior art and not being energy efficient, nor simplified. US 2018/092630 A recites a system including at least one piezoelectric transducer array having a plurality of piezoelectric transducer elements. The array is typically tilted and aimed at blood vessel measurements. EP 3 384 851 A1 recites a bladder monitoring system comprising a wearable bladder monitoring device. US 2017/0258386 A1 recites a wearable ultrasound device for signaling changes in human or animal body, and use of such a wearable device for signaling over a prolonged period of time. In an example the changes occur in a bladder. The documents are mostly silent on the nature of acoustic pulse sources, and timing thereof. None of these documents mentions significant simplification or measures to limit energy consumption of the electronics.

For certain devices using ultrasound for determining or monitoring a liquid volume in a cavity, such as in a body, the ultrasound may need to be provided under an angle, relative to an orientation of the device. Especially and in so far as mature people are concerned bones in the pelvic girdle, such as the pubic bone, may obstruct ultrasound; the device then typically needs to be placed above the pubic bone, and needs to transmit and receive ultrasound under an angle.

In general, for prolonged use, devices, and in particular small wearable devices, such as a bladder monitor, need to use minimal amounts of energy, as typically the power source is "on board" of the device and it should be recharged as little as possible. Electronic circuits of the prior art ultrasound technology are dedicated to obtain as much and as detailed information as possible, typically using sophisticated electronics and software, e.g. with dynamic focusing for high-quality imaging. However, energy consumption of such device is relatively large, which is not much of a problem if such devices are wired to the grid, but is a problem, in view of operation time, for stand-alone devices.

Therefore, there still is a need for an improved array which may be used in an ultrasound device, which overcomes one or more of the above disadvantages, without jeopardizing essential functionality and advantages.

SUMMARY OF THE INVENTION

The present invention relates in a first aspect to an energy efficient simplified analogue phased array transducer for ultrasound beam steering, in a second aspect to a product, such as a small wearable ultrasound device for signalling changes in a human or animal body, such as a liquid volume in a body cavity of a human or an animal, in a third aspect to a use of said product, and in a fourth aspect to a method of operating an ultrasound product.

The present phased array provides a decrease in energy consumption by for example more than 75%, and typically more than 80%, such as more than 85%, at the receiving side of the transducer array. Also, the complexity of a receiving circuit may be reduced, such as by using less than 50%, or even 15% of the components in a comparable prior art phased array electronic circuit. It is noted that for various applications a reduction in details of information obtained by the transducer array is acceptable. For instance, non-imaging applications, like recognizing a volume of a cavity and an amount of liquid in said cavity is found to be achievable in combination with the above significant reduction in components and in energy consumption. The present array comprises an array of n*m transducers elements operating a frequency of 20 kHz-50 MHz, typically 100 kHz-20 MHz, preferably 500 kHz-15 MHz, wherein at least two neighbouring transducers elements are at a mutual distance of approximately 0.5 wavelength (0.5λ±10%), preferably 0.5λ±5%, more preferably 0.5λ±3%, preferably comprising at least 1*m transducers, transmission control electronics for beam steering of the array comprising at least one high-voltage pulse source, wherein sources are linked to a low-voltage timing circuit for timing of the at least one pulse sources, simplified receiving control electronics adapted to limit energy consumption when processing received ultrasound, and an electrical power source in electrical connection with the array or an electrical connection for providing electrical power to the array. The at least one high-voltage pulse source may have a voltage of >12V, such as 20-200 V, e.g. 30-50 V, whereas the low-voltage timing circuit may have a voltage of <5.5V for timing of the at least one high-voltage pulse sources, such as 0.5-3.3 V. The array may be relatively small, with lesser components than used in prior art ultrasound imaging, limiting energy consumption and component amount, and may comprise one or more rows n. As arrays may be relatively small, a space occupied by said arrays can also be relatively small. The rows of arrays, if applied for e.g. a bladder scan, are oriented such that a phased array provides beam steering under an angle relatively to the (longitudinal) axis of the row(s). For addressing the transducers in a phase mode, and for receiving and addressing receiving arrays, a controller is provided. The controller may perform further functions. The present invention makes use of energy reduction measures to reduce energy consumption when processing received ultrasound.

In the present phased array transducer the receiving control electronics is selected from (i) at least one and preferably more than 2 and at maximum all ultrasound receiving transducer element are adapted for determining ultrasound energy in connection with a rectifying amplifier and the rectifying amplifier in connection with an analogue adder for adding the outputs of the rectifying amplifiers, (thus avoiding the power consumption of all beam steering electronics for reception) (ii) <50%, preferably <20%, of the n*m transducer elements connected or connectable to receive electronics, (wherein not-connected transducer elements are void of receiving electronics, thus avoiding most of the power consumption of the receive electronics), and (iii) combinations thereof.

In a second aspect the present invention relates to a product comprising a phased array transducer according to the invention, wherein the product is preferably selected from a wearable device, a portable device, a medical device, a non-destructive testing device, and combinations thereof. If the product is a non-destructive testing device it can use the energy efficient simplified phased array to enable beam steering at arbitrary angles at low energy and lower complexity and cost than prior art products. In an exemplary embodiment said product is a small, typically wearable, wireless ultrasound device for signalling a change in a body tissue, body vessel or body cavity, such as a bladder, preferably a stand-alone device.

In the context of the present invention the term "small" in combination with the present product relates to a size, indicating that the present product maybe worn for a prolonged period of time without relevant discomfort for a user thereof and that it is preferably (nearly) invisible when worn under clothes. The term "wireless" indicates that there is no electrical conductor connecting the present product to an outside world; the term "wearable" indicates that a user of the product can move freely. As a consequence of the product being small, wearable and wireless it can be worn and likewise is portable and wearable e.g. without limiting movement of the user. Further, a body cavity relates to a fluid (liquid/gas)-filled space in an animal or human other than those of vessels (such as blood vessels and lymph vessels). Further, position is taken to be a general term for a configuration of the human body, whereas the term posture relates to an (un)intentionally or habitually assumed body position. Typical positions are e.g. standing, sitting, squatting, crouching, kneeling, lying. Other positions, such as atypical positions and stress positions fall under the term as well. The term "(semi-)continuously" is used to indicate that monitoring and signalling can take place over a prolonged period of time; during said period of time at any given moment monitoring/signalling may occur; however, typically during said period of time the product is in an idle mode at least part of the time; it preferably is taking active measurements only at specific and selected moments. In view of "calculating" it is noted that often a precise outcome is questionable; in such cases the term may refer to "estimating".

The present device or product can be used for permanent and semi-permanent measurements, or monitoring. It can also be contacted to a body in a permanent or semi-permanent mode; thereto contacting means should preferably be compatible with a human skin, e.g. in terms of toxicity, irritation, adhesion, form stable over time, etc.

In a third aspect the present invention relates to a use of the present product for determining or monitoring a liquid volume in a cavity, such as a bladder, a uterus (amniotic fluid), a sinus, a pleural cavity, a pericardial sac, and a vessel such as an aorta, for detecting or monitoring at least one of aneurism, infection, tumour, dehydration, pleural effusion, urine in-flux rate from at least one kidney, hydrocephalus, a size of a human or animal cavity, for determining a liquid volume in a lung, for training, for ultrasound image forming, as a flow sensor, for (semi)continuous monitoring over longer periods of time, for monitoring during normal life, and for monitoring inside or outside a hospital or in a (long-term) care-taking environment, optionally in combination with a further (second) sensor or product.

In a fourth aspect the present invention relates to a method of operating an ultrasound product according to the invention, comprising the steps of determining an amount of liquid in a bladder, based on the amount determined, performing a further act, or refraining from further action.

Details of said product, use thereof, and method of operating can be found in WO 2016/085341 A2, of which the specification and claims are incorporated herein by reference.

Thereby the present invention provides a solution to one or more of the above-mentioned problems.

Advantages of the present invention are detailed throughout the description.

DETAILED DESCRIPTION OF THE INVENTION

The present invention relates in a first aspect to an energy efficient simplified phased array transducer for ultra-sound beam steering according to claim 1.

As a reference, FIG. 9a (identical to FIG. 2) shows the standard, prior art, analog beam steering electronics in reception. In an exemplary embodiment of the present phased array transducer rectifying amplifiers, these amplifiers are selected from circuits like a diode, a quadratic amplifier, a convertor for converting a negative amplitude into a positive amplitude and for maintaining a positive amplitude, a logarithmic amplifier, and variations thereof, and combinations thereof. Results of adding the outputs of these rectifying amplifiers is shown in FIG. 5, and the schematic with rectifying amplifiers is shown in FIG. 9b.

In an exemplary embodiment of the present phased array transducer the receiving control electronics is adapted to optimize beam steering in reception, for at least two, and preferably not all, ultrasound receiving transducer elements, spread over the width of the transducer to optimize the beam width without introducing strong grating lobes at angles where the intensity of the ultrasound transmit beams is strong. The schematic with beam steering electronics in reception, but with reduced number of transducer elements connected, is shown in FIG. 9c.

An example of a combination of a reduced number of channels and rectifying amplifiers is shown in FIG. 9d.

In case of non-rectifying amplifiers, an exemplary embodiment of the present phased array transducer may have the analogue adder adapted to add the amplitude of the positive phase and the amplitude of the negative phase of the received signal, such as can be seen in FIG. 5.

In an exemplary embodiment the present phased array transducer may comprise one high-voltage pulse transmission source per transducer, wherein sources are preferably identical.

In an exemplary embodiment the present phased array transducer may comprise a voltage controller for applying a voltage to the transducer.

In an exemplary embodiment of the present phased array transducer the receiving control electronics is connected or connectable to <50% of the receiving transducer elements (FIGS. 6-7), such as <20% of the receiving transducer elements, as shown in FIG. 9C.

In an exemplary embodiment of the present phased array transducer connected or connectable receiving transducer elements are selected such that k not-connected transducer elements are in between the connected transducer elements, wherein k is selected from 1-7 (FIG. 6), preferably wherein k is 2-6, more preferably wherein k is 3-5, such as k is 3. For some cases at k is 3, the largest side lobes in transmit directionality are compensated by a minimum in the receive directionality, making this choice preferred in certain cases.

In an exemplary embodiment of the present phased array transducer $n \in [1-10]$ and $m \in [2-1024]$, preferably wherein $n \in [1-3]$ and $m \in [4-128]$, more preferably wherein $n \in [1-3]$ and $m \in [8-48]$, even more preferably wherein $n \in [1,2]$ and $m \in [16-36]$, such as $n \in [1]$ and $m \in [24-32]$.

In an exemplary embodiment of the present phased array transducer elements comprise a MEMS, such as a CMUT and PMUT, bulk piezo material, such as ceramic and crystalline material, piezocomposite, active piezoelectric material, ferroelectric ceramic, and combinations thereof.

In an exemplary embodiment of the present product the transducers elements are capable of operating separately, sequentially, in phase-shift mode, in parallel mode, in spatial scan mode, in intensity mode, in pulsed mode, in harmonic mode, variations thereof, and combinations thereof.

In an exemplary embodiment the present phased array transducer may comprise at least one series of m transducer elements over a length, wherein each of the electrodes on one side of all m transducer elements are connected electrically to the respective transducer electronics, and wherein the (counter-)electrodes on the other side are i) all connected together (FIGS. 8a,b), or ii) the electrodes on the other side are split in two halves, where half of each electrode length is connected to a first electrode connector and the other half electrode length is connected to a second electrode convector, (to allow separate activation of the two halves, e.g. applying two different acoustic lenses (e.g. prisms or focusing lenses) on these two separate halves of the transducer array FIGS. 8c,d), or iii) a $p^{th}$ fraction of p≥3 of the electrode length is connected to a $p^{th}$ electrode connector, wherein p preferably $\in [3-5]$, perpendicular to the long transducer elements, allowing even more different lenses, or iv) combinations thereof.

In an exemplary embodiment of the present product the product is a small wireless ultrasound product for signalling a change in a body tissue, body vessel or body cavity, such as a bladder, preferably a stand-alone product.

In an exemplary embodiment the present product may comprise at least one transducer director, for directing the generating and/or detecting means, capable of determining if a given transducer is placed in a correct position. Such an alignment using the directing means, for instance using beam steering, may be done using reference points in the body, such as the sacrum, the rectum, the pubic bone or, in women, the cervix. To enable (electronic) fine tuning of the alignment during use (with all postures of normal life) the transducer can contain more than m transducer elements (m+x) in one direction, where only the upper m elements or the lower m elements, or any m elements in between, are connected to transmission electronics, thus shifting the beam by the distance of, at maximum, x transducer elements for fine tuning of the alignment.

In an exemplary embodiment the present product may comprise a positioner for maintaining the product in a position, preferably at least one sensor for determining posture of a body of a user, a contacting means for contacting the product to a skin of the body, an energy scavenger, an ADC for converting analogue array signals to digitized output signals, wherein the product is wearable and is substantially flat. The present product can be tailored, e.g. such that desired frequencies and/or powers can be obtained. The product typically comprises at least one processor for controlling the product, such as for manipulating the transducer for providing a pulse and/or for determining a reflected pulse, switching the product on/off, etc. Optionally the processor is used for one or more of processing data, generating acoustical signals, and data communication. The product may comprise an electrical power provider in connection with the transducer, transceiver and processor, such as a battery, a capacitor, an energy scavenger, and combinations thereof. The electrical power provider may be of flexible nature, such that it can adjust to a curvature of a body to which the present product is attached, e.g. enhancing comfort for the wearer. The product comprises a positioner for maintaining the product in a position. It has been found that for reliable measurements, in line with the contacting means, the product should be kept in position; a small deviation over time, such as a few millimetres with respect to an original position is acceptable in this respect; so, some tolerance is present.

In an example of the present product the product the electronics therein is one or more of an IC, an ASIC, a printed circuit board (PCB), and variations thereof and combinations thereof.

In an example of the present product the transducer is one or more of a MEMS (CMUT or PMUT), a piezoelectric (ceramic or crystalline), and combinations thereof. It is preferred a very small product, in view of costs, manufacturability, ease of wear, replaceability, etc.

In an exemplary embodiment the present product may comprise a movement sensor, such as an accelerometer, gyroscope, and a magnetic sensor.

In an exemplary embodiment of the present product the wearable product consists of one integrated package.

The invention is further detailed by the accompanying figures and examples, which are exemplary and explanatory of nature and are not limiting the scope of the invention.

SUMMARY OF FIGURES

FIGS. 5a-f: Calculated amplitude traces.

FIG. 6: The width of the transmit-receive sensitivity (thick lines) and the maximum height of the side lobes, relative to the centre peak (thin lines).

FIG. 7: The width of the transmit-receive sensitivity (thick lines) and the maximum height of the side lobes, relative to the centre peak (thin lines).

FIGS. 8a-d show possible array layouts according to exemplary embodiments.

FIGS. 9a-d show several options to simplify and to limit energy consumption, compared to the standard beam steering approach in reception, according to exemplary embodiments.

DETAILED DESCRIPTION OF FIGURES

Figure 1:
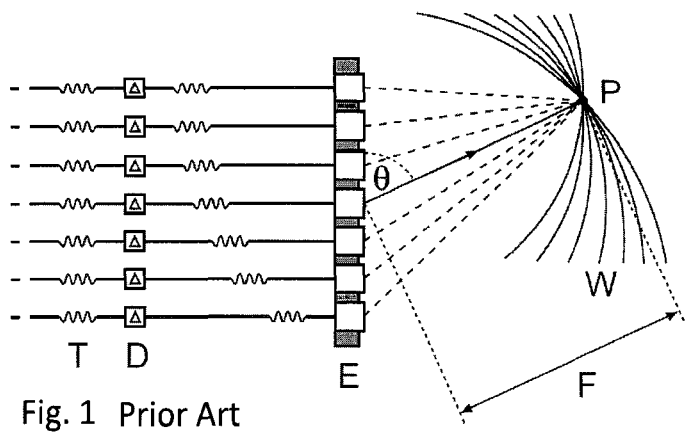
FIG. 1. Schematic set-up of part of a prior art transmitting device.

FIG. 1: Transmit pulse formation by a phased array to a focal point, as used in the prior art. For this purpose a voltage pulse is provided to each transducer element E with a well-defined delay D so as to form a beam focus at the desired point P.

Figure 2:
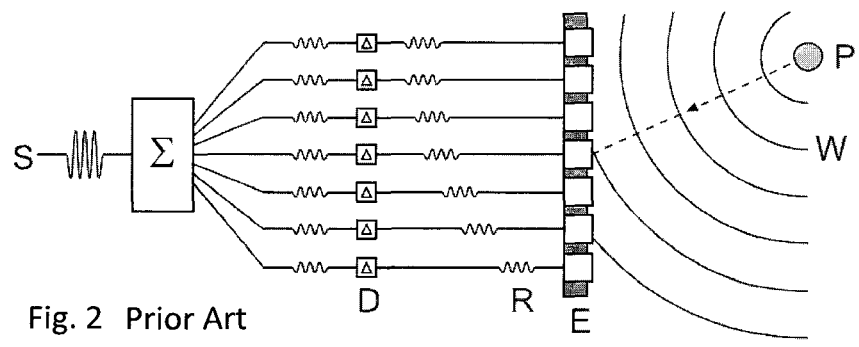
FIG. 2: Schematic set-up of part of a prior art receiving device.

FIG. 2: Reception of reflections from a focal point by a phased array, as used in the prior art. The delay of each signal makes that all signals arrive at the same time at the summation.

Figure 3:
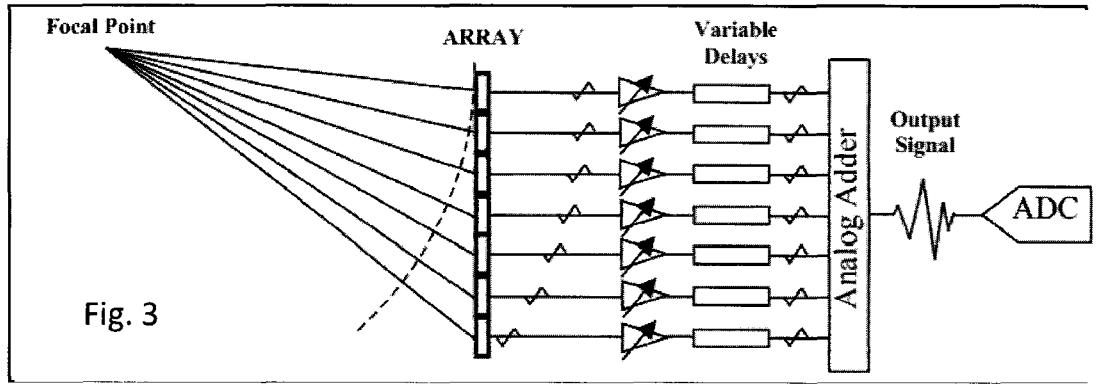
FIG. 3: Analog beam forming principle.

FIG. 3: Analog beam forming principle, where the delays are made in the analogue domain, before the analogue summation and the analogue-to-digital conversion, as used in the prior art.

Figure 4:
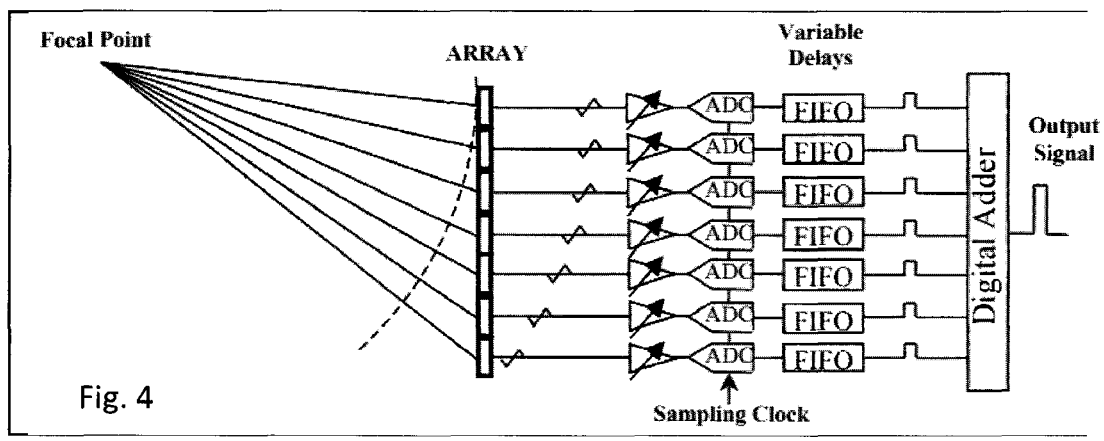
FIG. 4: Digital beam forming principle.

FIG. 4: Digital beam forming principle, where each signal is first digitized by an analogue-to-digital converter and then the delays are added during signal processing in the digital domain, as used in the prior art.

FIGS. 5a-f: Calculated amplitude traces for ultrasound beams coming from various directions (8 (a), 16 (b), 24 (c), 33 (d), 42 (e) and 54 (f) degrees, respectively) for three approaches to construct these data (not rectified "interfering data", rectified "abs(data)" and negative values made zero "pos(data)") and one reference line ("conventional beam steering") with interference and the optimal delays in reception, as known from the prior art.

The receive beam steering approach, with four (of e.g. 24) receiving transducers with non-receiving transducer elements in between has been extended in FIG. 6, where all possibilities are elaborated. From this figure, it appears that three non-receiving transducer elements between the receiving ones is the optimal configuration when using only four transducer elements for reception of the ultrasound. This results in an array of 24 transducer elements, where all 24 transducers are used for sending and only transducer Nr. 6, 10, 14 and 18 are used for receiving the ultrasound. It is observed that that the directional angle of the first (and largest) side lobe in transmission coincides with the angle of the first minimum in reception, reducing the side lobes in the transmit-receive sensitivity considerably. As a reference we show a phased array with 24 transducers sending: The dotted line denotes a single receiving transducer element and the dashed line denotes all 24 receiving. Note that the number of 24 elements is only used as an example to show the principle. Different optimizations may apply for different number of elements.

The receive beam steering approach, with transducers with three non-receiving transducer elements in-between has been extended in FIG. 7, where the number of transducer elements has been varied, keeping their distance fixed. From this figure, it appears that five receiving transducers with three non-receiving transducer elements between the receiving ones is the optimal configuration in this example. This results in and array of 24 transducer elements, where all transducers are used for sending and only transducer Nr. 4, 8, 12, 16 and 20 are used for receiving the ultrasound. As a reference we show a phased array with 24 transducers sending: The dotted line denotes a single receiving transducer element and the dashed line denotes all 24 receiving.

FIGS. 8a,b show an array connected with one electrical contact at the bottom side and ten at the top (top and bottom view) and FIGS. 8c,d show an array connected with two electrical contact at the bottom side and ten at the top (top and bottom view).

FIGS. 9a-d show examples of the standard, prior art, beam steering approach in reception (FIG. 9a), the approach with rectifying amplifiers selected from circuits, like a diode, a quadratic amplifier, a convertor for converting a negative amplitude into a positive amplitude and for maintaining a positive amplitude, a logarithmic amplifier, and variations thereof, and combinations thereof (FIG. 9b), the approach of beam steering with a reduced number of transducer elements connected (FIG. 9c) and a combination of the above (FIG. 9d).

Figure 10A:
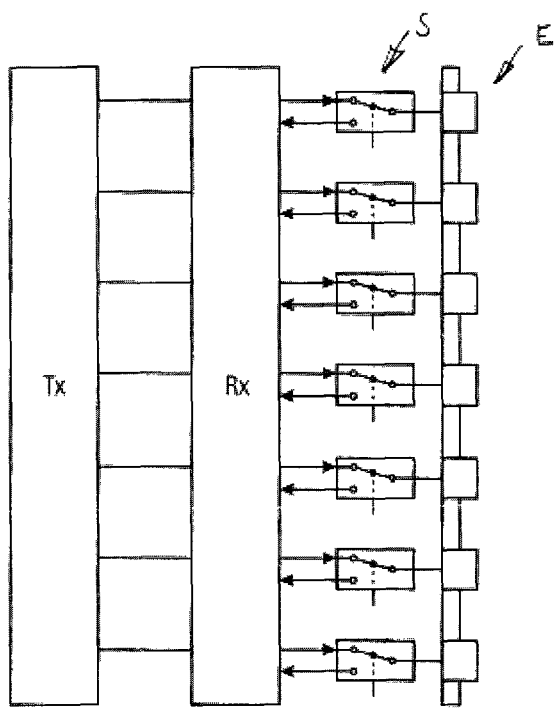
FIGS. 10a-c show some options for connecting only a fraction of the available transducer elements to the receiving circuit according to respective embodiments.
Figure 10B:
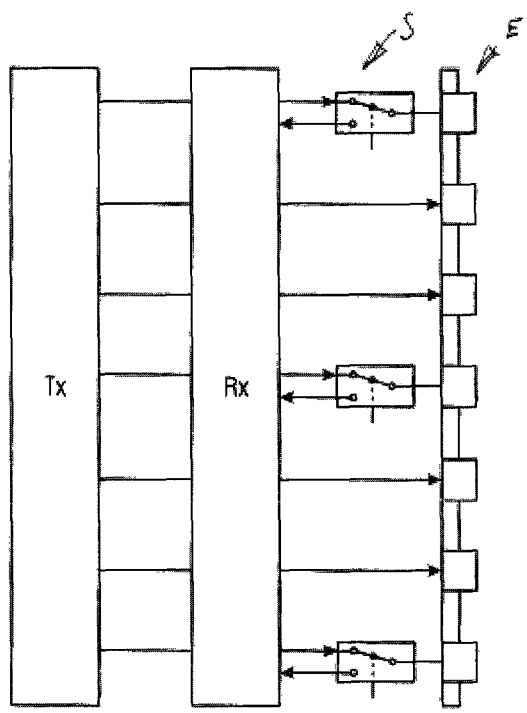
Figure 10C:
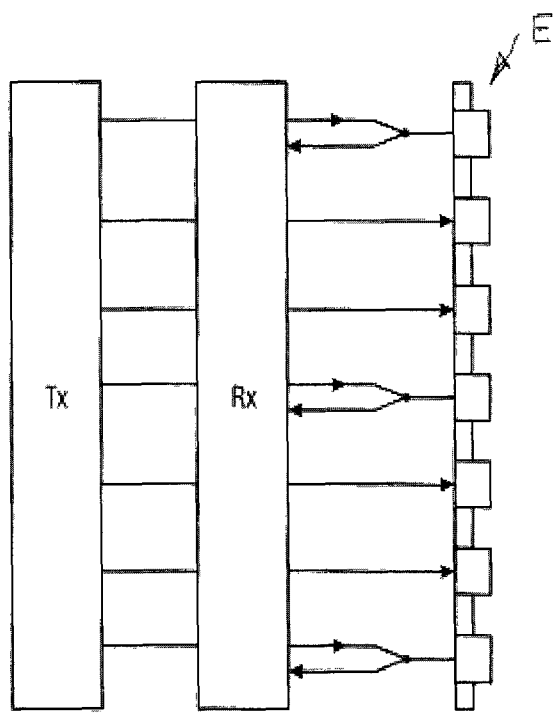

FIGS. 10a-c show some concepts of operating or connecting only a fraction of the available transducer elements to the receiving circuit according to respective embodiments. In such a configuration of a pulse echo ultrasound system the transducer acts as both transmitter and receiver. The transducer can be activated by a pulse of high voltage, typically 25 to 150 volts and short duration, typically 100 to 500 nano-seconds and the receiver will receive a voltage of less than 1 volt, typically in the millivolt range.

In FIG. 10a shows an embodiment in which the plurality of transducer elements E is connected to both a transmission circuit Tx as well as to a receiving circuit Rx over corresponding switches S. The respective operation, i.e. transmission or reception, is set by operating the switches S accordingly. In an embodiment, all, or a relatively large number of the transducer elements are switched to the transmission circuit during the transmission phase, whereas only a part, or a relatively small number of the transducer elements are switched to the receiving circuit during the receiving phase. In this way, an energy saving mode may be implemented by solely controlling the switches S accordingly, while maintaining in principle the capability of using all transducer elements during the receiving phase.

The option shown in FIG. 10b shows an embodiment in which only a reduced number of switches S are provided for those transducer elements that are actually used during the receiving phase. This embodiment may further contribute to reducing the element count and circuit complexity of the receive electronics, besides providing the advantages relating to energy and power saving, especially during receiving.

FIG. 10c shows an embodiment wherein both transmit and receive electronics are directly coupled to the transducer elements without any switch in between. This is possible in case the output resistance of the pulsers is sufficiently high, such as >1 MΩ, so that no current will flow (typically <1 µA), when the receive signal comes in. This embodiment may further contribute to reducing the element count and circuit complexity even further by avoiding the switches S from FIG. 10a. and FIG. 10b.

The invention although described in detailed explanatory context may be best understood in conjunction with the accompanying examples and figures.

The invention claimed is:

1. A wireless, wearable ultrasound device for signaling a change in or determining a volume of a user's bladder using a phased array transducer for ultrasound beam steering comprising:
an array of n*m transducer elements operable at a frequency of 20 kHz-50 MHZ,
transmission control electronics for beam steering of the array, comprising at least one high-voltage pulse source operating at a voltage of greater than 12 volts, wherein said at least one pulse source is linked to a low-voltage timing circuit operating at a voltage of less than 5.5 volts, for timing of the at least one pulse source,
receiving control electronics arranged to limit energy consumption when processing received ultrasound, wherein less than 20% of the n*m transducer elements are configured for connection to the receiving control electronics and available for operation as ultrasound receiving transducer elements, and
an electrical power source in electrical connection with the array for providing electrical power to the array.

2. The device according to claim 1, comprising a rectifying amplifier and an analogue adder wherein at least one and preferably all ultrasound receiving transducer elements are adapted for determining ultrasound energy in connection with the rectifying amplifier and the rectifying amplifier is in connection with the analogue adder for adding the outputs of the rectifying amplifiers.

3. The device according to claim 2, wherein the rectifying amplifier is selected from the group of circuits consisting of: a diode, a quadratic amplifier, a convertor for converting a negative amplitude into a positive amplitude and for maintaining a positive amplitude, a logarithmic amplifier, and variations thereof, and combinations thereof.

4. The device according to claim 1, wherein the receiving control electronics is arranged to optimize beam steering in reception for at least two ultrasound receiving transducer elements.

5. The device according to claim 2, wherein the analogue adder is arranged to add an amplitude of a positive phase and an amplitude of a negative phase of a received signal.

6. The device according to claim 1, comprising one high-voltage pulse transmission source per transducer element.

7. The device according to claim 1, comprising a voltage controller for applying a voltage to the transducer elements.

8. The device according to claim 1, wherein the ultrasound receiving transducer elements are arranged such that k not-connected transducer elements are positioned in between the ultrasound receiving transducer elements, wherein k is selected to be a number from 1-7.

9. The device according to claim 1, wherein n is from 1 to 10 and m is from 2 to 1024.

10. The device according to claim 1, wherein the transducer elements comprise a MEMS, bulk piezo material, piezocomposite, active piezoelectric material, ferroelectric ceramic, or combinations thereof.

11. The device according to claim 1, comprising at least one series of m transducer elements having electrodes on a first side and counter electrodes on a second side, wherein each of the electrodes of all m transducer elements are connected electrically to the respective transducer electronics, and wherein the counter electrodes on the second side are all mutually connected together or the counter electrodes are split in p fractions along a length of the electrode and each $p^{th}$ fraction is connected to a $p^{th}$ electrode connector perpendicular to the length.

12. The device according to claim 1, wherein the transducer elements are arranged to be operated separately, sequentially, in phase-shift mode, in parallel mode, in spatial scan mode, in intensity mode, in pulsed mode, in harmonic mode, variations thereof, and combinations thereof.

13. The device according to claim 1, wherein both the transmission control electronics and the receiving control electronics are directly coupled to the transducer elements and an output resistance of the transmission control electronics is greater than 1 megaohm.

14. The device according to claim 1, comprising at least one transducer director for aligning the phased array transducer with the body of a user during use or a positioner for maintaining the device in position on the body of a user.

15. The device according to claim 14, further comprising one or more of: at least one sensor for determining posture of a body of a user, a contacting means for contacting the device to a skin of the body, an energy scavenger, and an ADC for converting analogue array signals to digitized output signals; wherein the device is substantially flat and preferably consists of one integrated package.

16. The device according to claim 1, comprising at least one of a movement sensor, an accelerometer, a gyroscope and a magnetic sensor.

17. The device according to claim 1, wherein the transmission control electronics and the receiving control electronics comprise one or more of an integrated circuit, a piezoelectric element, a printed circuit board and combinations thereof.

18. The device according to claim 1, wherein all of the less than 20% of the n*m transducer elements configured for connection to the receiving control electronics are connected.

19. A method for signaling a change in or determining a volume of a user's bladder using a phased array transducer for ultrasound beam steering, the method comprising:
  providing an array of transducer elements;
  aligning the array of transducer elements with a portion of a body of a user adjacent to the bladder;
  operating a high-voltage pulse source at a voltage of greater than 12 volts and a frequency of 20 kHz-50 MHz to drive the transducer elements as a phased array, wherein transmission control electronics is provided for beam steering of the array towards the bladder, wherein the at least one pulse source is linked to a low-voltage timing circuit operating at a voltage of less than 5.5 volts, for timing of the at least one pulse source, and
  detecting a pulse echo from a wall of the bladder with a fraction of the transducer elements, wherein less than 20% of the transducer elements are configured for connection to receiving control electronics, are connected and available for operation as ultrasound receiving transducer elements.

20. The method according to claim 19, further comprising directing the array by selecting a sub-group of transducer elements for operation in transmission.

* * * * *